United States Patent [19]

Eberbach

[11] Patent Number: 5,122,155

[45] Date of Patent: Jun. 16, 1992

[54] HERNIA REPAIR APPARATUS AND METHOD OF USE

[76] Inventor: Mark A. Eberbach, 4232 Winding Willow Dr., Tampa, Fla. 33624

[21] Appl. No.: 746,707

[22] Filed: Aug. 19, 1991

Related U.S. Application Data

[63] Continuation-in-part of Ser. No. 667,456, Mar. 11, 1991, which is a continuation-in-part of Ser. No. 595,956, Oct. 11, 1990.

[51] Int. Cl.⁵ ............................................. A61F 2/00
[52] U.S. Cl. ................................. 606/213; 606/1; 606/151
[58] Field of Search ............... 606/110, 113, 114, 127, 606/151, 200, 213, 1; 604/11-15; 623/12; 128/887

[56] References Cited

U.S. PATENT DOCUMENTS

| | | | |
|---|---|---|---|
| 460,940 | 10/1891 | Baugh | 606/106 |
| 1,275,520 | 8/1918 | Bell | |
| 3,152,466 | 10/1964 | Williams | 68/214 |
| 3,706,311 | 12/1972 | Koka | |
| 3,874,388 | 4/1975 | King et al. | 623/11 |
| 4,007,743 | 2/1977 | Blake | 623/11 |
| 4,347,847 | 9/1982 | Usher | 606/151 |
| 4,519,643 | 5/1985 | Harris | 294/19.1 |
| 4,557,255 | 12/1985 | Goodman | 128/7 |
| 4,744,364 | 5/1988 | Kensey | 606/213 |
| 4,769,038 | 9/1988 | Bendayid et al. | 606/151 |
| 4,779,616 | 10/1988 | Johnson | |
| 4,813,978 | 10/1989 | Ginsburg | |
| 4,909,789 | 3/1990 | Taguchi | 604/107 |
| 4,964,417 | 10/1990 | Peters | 128/887 |
| 5,021,059 | 6/1991 | Kensey et al. | 606/213 |

FOREIGN PATENT DOCUMENTS

53-94481  8/1978  Japan.

OTHER PUBLICATIONS

Francis E. Stock, "Repair Of Large Herniae With Nylon Mesh", The Lancet vol. CCLXVI #6808, Feb. 20, 1954 p. 395.

Primary Examiner—Stephen C. Pellegrino
Assistant Examiner—Glenn K. Dawson
Attorney, Agent, or Firm—Dominik, Stien, Saccocio, Reese, Colitz & Van Der Wall

[57] ABSTRACT

A method and apparatus for use by a surgeon to repair a weakened, deranged portion of the anatomy of a patient comprising a sheath having a distal end positionable within a patient and a proximal end positioned exterior thereof for manipulation by a surgeon, the sheath being of a length to extend from exterior of a patient through a laparoscopic opening into a surgical cavity of the patient; a prothesis movable from interior of the sheath to a location adjacent to the deranged portion to be repaired, the prothesis having an elongated passageway located adjacent to the periphery thereof; and an introducer positioned within the sheath and having a distal end coupled to the prothesis, the introducer adapted to effect the movement of the prothesis from interior of the sheath to exterior thereof and to expand the prothesis to a functionally expanded orientation adjacent to the part to be repaired.

6 Claims, 5 Drawing Sheets

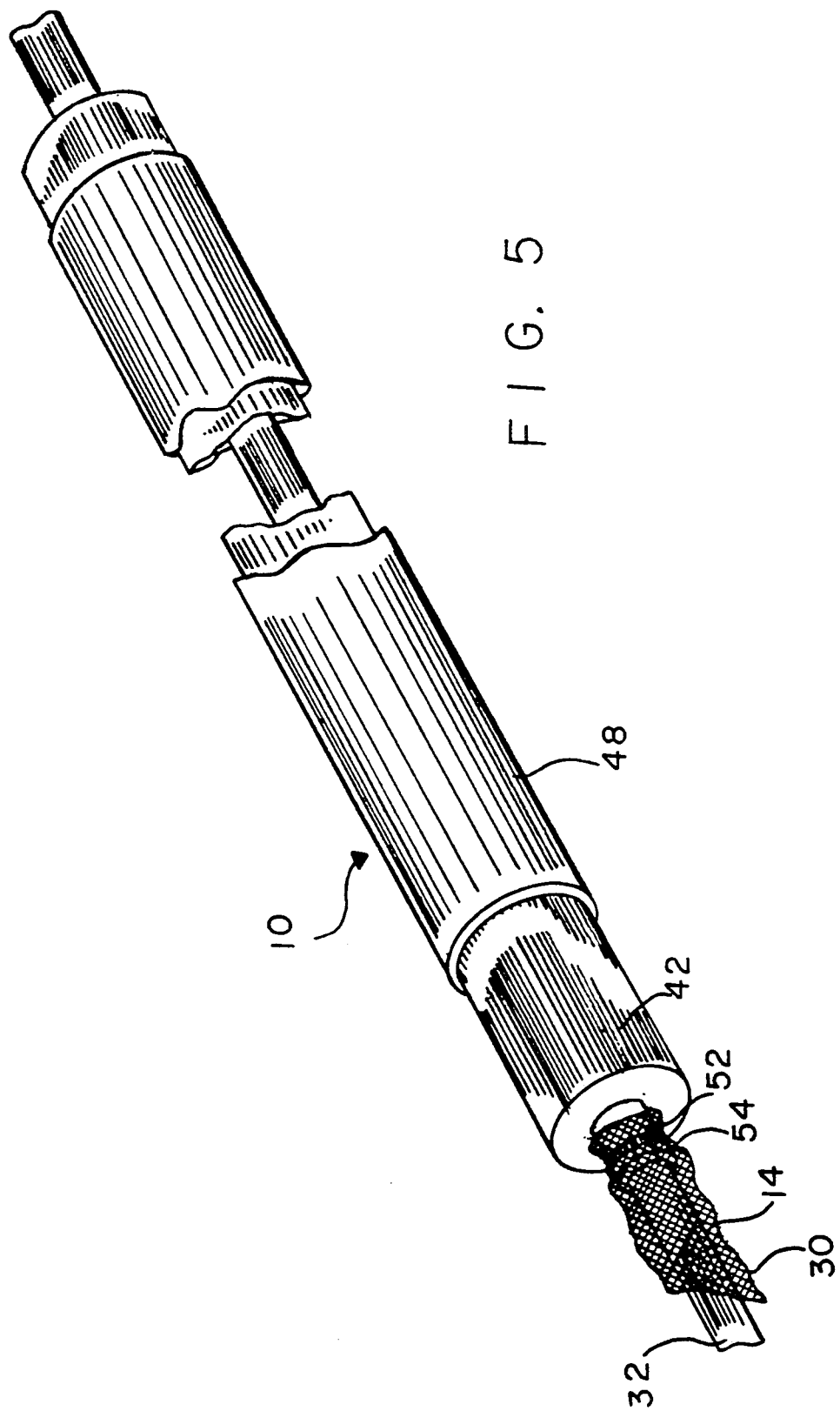

HERNIA REPAIR APPARATUS AND METHOD OF USE

RELATED APPLICATION

This application is a continuation in part application of copending U.S. patent application Ser. No. 07/667,456 filed Mar. 11, 1991 which, in turn is a continuation in part application of copending U.S. patent application Ser. No. 07/595,956 filed Oct. 11, 1990.

BACKGROUND OF THE INVENTION

1. Summary of the Invention

This invention relates to a surgical apparatus and method and, more particularly, to the repair of hernias with a laparoscopic approach employing patches wherein only the patch remains in the operation site after the operation.

2. Summary of the Background Art

A hernia is one of the most common ailments of mankind. Approximately five percent of the adult male population is affected. Basically, a hernia is a weakness or hole in the abdominal wall through which abdominal contents such as bowels may protrude. Inguinal or groin hernias normally occur at one or more of three locations. The first location is in the weakened wall of inguinal floor of the abdomen in Hesselfbach's triangle. This type of hernia is called a direct hernia. An indirect hernia occurs at the internal ring adjacent to the vas deferens as it exits the abdomen to become part of the spermatic cord. The third is a femoral hernia that occurs adjacent and medial to the femoral blood vessels.

All hernias represent a potentially life threatening condition and once diagnosed they should be repaired unless there is some contraindication.

The surgical repair of an inguinal hernia (inguinal herniorrhaphy) is a common procedure which surgeons often perform on an outpatient basis. It is estimated that 500,000 are performed each year in the United States. According to the procedure, an anesthetic is first administered to the patient and the surgeon then makes a large incision, about 6 inches, in the patient just above the inguinal ligament. Supporting abdominal muscles and fascia are dissected to reveal the hernia sac. The herniated contents protruding through the opening in the abdominal wall are returned to the abdomen. Thereafter, the surgeon closes the hernia sac. The local tissues are then sutured together from opposite sides of the weakened tissue, hole or hernia. The stretched or otherwise weakened tissue may be cut away. Where appropriate, a patch of artificial material may be sutured to the normal tissue to replace the stretched or otherwise weakened tissue or to reenforce over the outside or inside of the repair. The incision is then closed over the repair. Recovery time necessary prior to heavy lifting or strenuous labor is usually six to eight weeks and recurrence rates may approach twenty percent.

Another more difficult approach which is less common, but more physiological, is to make an incision in the abdomen superior or cephalad to the hernia. The surgeon cuts through the abdominal wall to the last layer (the peritoneum). Dissection continues in this preperitoneal approach and exposes the hernia defect from the inside. Again direct suture repair or patch repair may be performed. The recurrence rates are low with an inside patch repair because increased intra-abdominal pressure only serves to force the patch more firmly into place to plug the hole similar to a drain plug in a bathtub.

Although common, the standard operational procedures for repair of a hernia is undesirably lengthy and, consequently, costly, requires a large incision with the excessive dissection of normal tissue, causes excessive pain and discomfort to the patient, involves unacceptably long recovery and work disability time, and results in an unacceptably high recurrence rate.

Accordingly, it is an object of the present invention to provide a method and apparatus for use by a surgeon to repair a weakened, deranged portion of the anatomy of a patient comprising a sheath having a distal end positionable within a patient and a proximal end positioned exterior thereof for manipulation by a surgeon, the sheath being of a length to extend from exterior of a patient through a laparoscopic opening into a surgical cavity of the patient; a prothesis movable from interior of the sheath to a location adjacent to the deranged portion to be repaired, the prothesis having an elongated passageway located adjacent to the periphery thereof; and an introducer positioned within the sheath and having a distal end coupled to the prothesis, the introducer adapted to effect the movement of the prothesis from interior of the sheath to exterior thereof and to expand the prothesis to a functionally expanded orientation adjacent to the part to be repaired.

It is a further object of the present invention to employ laparoscopic techniques for the repair of hernias thereby reducing the length of the incision along with the unnecessary dissection of normal tissue.

It is a further object of the present invention to utilize a new laparoscopic approach via the preperitoneal space in addition to the intraabdominal space.

It is a further object of the present invention to minimize the time and cost of hernia operations.

It is a further object of the present invention to minimize a patient's pain and discomfort associated with a hernia operation.

It is a further object of the present invention to shorten the recovery time normally attendant with a hernia operation.

It is a further object of the present invention to reduce or preclude the recurrence of hernias.

It is a further object of the present invention to provide a delivery system for prosthetic materials.

Further objects of the present invention are to internally patch and restore stretched or weakened ares of an abdominal wall or overt hernia defects and to simultaneously patch all primary and secondary abdominal areas which are predisposed to hernias.

Lastly, it is an object of the present invention to utilize a patch for the repair of a hernia wherein the patch only remains in the repaired area after laparoscopic surgery.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

The invention is defined by the appended claims with specific embodiments shown on the attached drawings. For the purpose of summarizing this invention, the invention may be incorporated into an improved laparoscopic apparatus for the repair of abdominal hernias by a surgeon through the patching of weakened portions of the abdominal part to be repaired comprising a patch positionable adjacent to the weakened portions of the abdominal part to be repaired, the patch having an elongated passageway located adjacent to the majority of the periphery of the patch, the passageway having an opening at one end thereof; an elongated interior ribbon having a distal end positioned through the opening of the passageway and slidable within the passageway; an elongated intermediate cylindrical plunger having an interior slidably receiving the ribbon, the plunger having a distal end coupled to the patch and a proximal end to be manipulated by the surgeon; and an elongated exterior cylindrical sheath having an interior slidably receiving the the plunger, the ribbon and the patch, the sheath having a distal end adjacent to the distal ends of the patch and a proximal end to be manipulated by the surgeon, the sheath being of a length to extend from exterior of a patient through a laparoscopic port into a surgical cavity which includes the part to be repaired.

The invention may also be incorporated into apparatus for use by a surgeon to repair a weakened, deranged portion of the anatomy of a patient comprising a sheath having a distal end positionable within a patient and a proximal end positioned exterior thereof for manipulation by a surgeon, the sheath being of a length to extend from exterior of a patient through a laparoscopic opening into a surgical cavity of the patient; a prothesis movable from interior of the sheath to a location adjacent to the deranged portion to be repaired, the prothesis having an elongated passageway located adjacent to the periphery thereof; and an introducer positioned within the sheath and having a distal end coupled to the prothesis, the introducer adapted to effect the movement of the prothesis from interior of the sheath to exterior thereof and to expand the prothesis to a functionally expanded orientation adjacent to the part to be repaired.

The prothesis is a patch. The introducer includes an elongated interior ribbon having a distal end positioned through an opening in a passageway of the patch and slidable within the passageway, the introducer also including an elongated intermediate cylindrical plunger having an interior slidably receiving the ribbon, the plunger having a distal end coupled to the patch and a proximal end to be manipulated by a surgeon. The ribbon is slidably removable from the patch.

Lastly, the invention may be incorporated into a method for the laparoscopic repair of abdominal hernias by a surgeon through the patching of weakened portions of the abdominal part to be repaired comprising the steps of providing a patch positionable adjacent to the weakened portions of the abdominal part to be repaired, the patch having an elongated passageway located adjacent to the majority of the periphery of the patch, the passageway having an opening at one end thereof; providing an elongated interior ribbon having a distal end positioned through the opening of the passageway and slidable within the passageway; providing an elongated intermediate cylindrical plunger having an interior slidably receiving the ribbon, the plunger having a distal end coupled to the patch and a proximal end to be manipulated by the surgeon; providing an elongated exterior cylindrical sheath having an interior slidably receiving the the plunger, the ribbon and the patch, the sheath having a distal end adjacent to the distal ends of the patch and a proximal end to be manipulated by the surgeon, the sheath being of a length to extend from exterior of a patient through a laparoscopic port into a surgical cavity which includes the part to be repaired; positioning the patch and the distal ends of the ribbon, plunger and sheath into a patient adjacent to the area to be repaired; advancing the patch and plunger from the sheath; advancing the ribbon into the passageway of the patch to expand the patch; coupling the patch to the area to be repaired; withdrawing the ribbon from the patch; separating the patch from the sheath; and withdrawing the ribbon, plunger and sheath from the patient.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 5 is a perspective illustration of the patch of the apparatus of the prior Figures and with parts broken away to show certain internal constructions thereof.

Similar reference characters refer to similar parts throughout the several views of the drawings.

DETAILED DESCRIPTION OF THE PREFERRED EMBODIMENT

Overview

Figure 1:
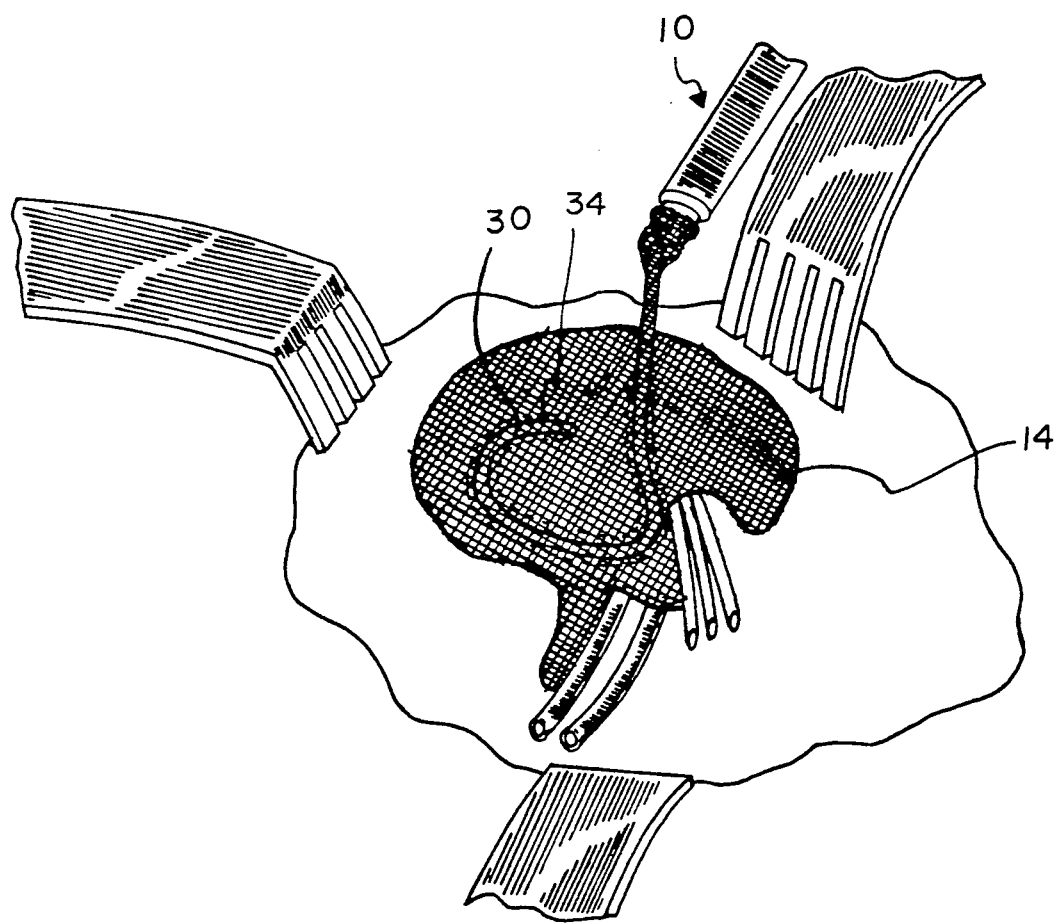
FIG. 1 shows a portion of the abdominal wall from the inside where hernias normally occur and also illustrating therein a patch for their repair and the precluding of further hernias.
Figure 2:
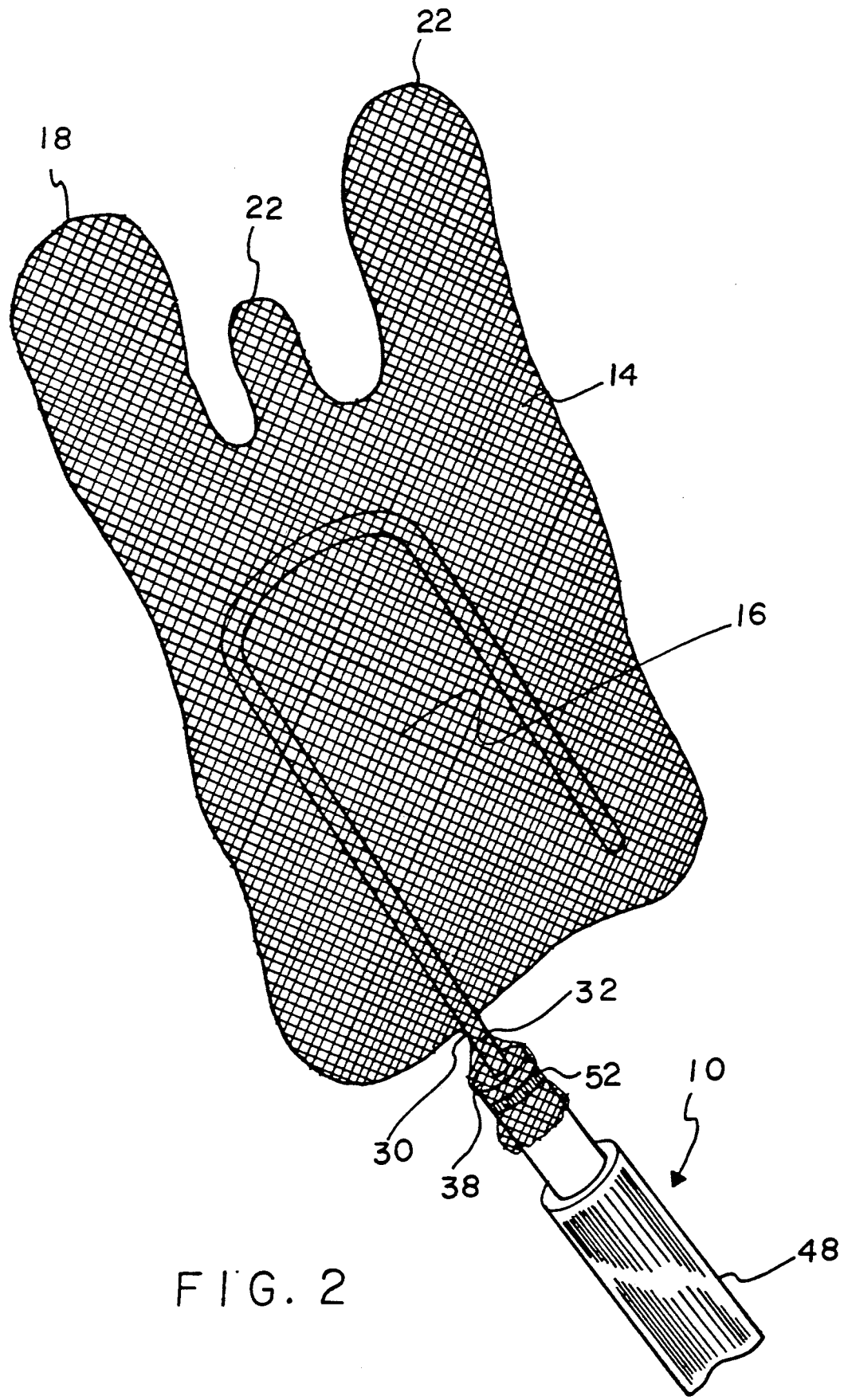
FIG. 2 is a perspective view of a patch constructed in accordance with the principles of the present invention similar to that shown in FIG. 1, illustrated in association with the patch is an introducer functioning as a delivery assembly and system for the patch.

Shown in FIG. 1 is that portion of the abdomen where hernias normally occur. Whether through old age, accident, personal abuse, congenital problems, or the like, the inguinal floor of the abdomen known as Hesselbach's triangle may become weakened to the point whereby inner abdominal contents such as a bowel may protrude. When the organ extending therethrough is a portion of the bowel, serious illness or even death may occur. This is a direct inguinal hernia. There are two other common types of groin hernias. These occur adjacent to either the vas deferens (indirect) or the femoral vessels (femoral hernia). When either the internal inguinal ring through which the vas deferens passes or the abdominal wall adjacent to the femoral vessels becomes enlarged, an opening is created through which abdominal contents such as intestines may protrude thereby constituting a hernia. In the past, surgeons operated upon the hernia area either from above (preperitoneal) or below (anterior) with large incisions which lead to great disability.

The present invention includes an introducer 10 with a prothesis which in the preferred embodiment is a patche 14, with the patche designed to cover all three areas where groin hernias normally occur and accomplishes a more physiological repair with a smaller incision utilizing laparoscopic technique by use of a specifically designed introducer and patch and preperitoneal approach presently not used. The prothesis is also adapted to be used on other deranged areas of a patient where repair is needed.

The patch 14 is a preferably fabricated of a mon-filament thread which is woven, knitted orotherwise formed into a fabric which is then cut to a shape. It has a main central portion 16 to cover the inguinal floor area where direct groin hernias normally occur. The shape is generally in the shape of a trapezoid with a major axis and a minor axis.

Extending outwardly from one edge are three asymmetrical portions, formed as thre fingers 18, 20 and 22 with the central finger being smaller than the other two. Formed between the fingers are spaced concave recesses, sized and positioned to be placed in close proximity to the vas deferens and or the femoral vessels. Those portions of the patch located adjacent to the recesses are thus adapted to cover those areas of the adomen where indirect and femoral hernias normally occur. At the same time, the central portion of the patch is adapted to cover the area of the inguinal floor where direct hernias normally occur.

The threads from which the patch is fabricated are of a surgically clean material which is durable, flexible, essentially inextensible and resistant to corrosion from bodily fluids. By way of example, one acceptable material is polypropylene such as Marlex mesh. Marlex is a trademark of the Johnson & Johnson Company of Sommerville N.J. Further, by way of example, one acceptable material thread is Nylon polymer. Nylon is a registered trademark of the E. I. DuPont deNemours Company of Wilmington, Del.

Formed into the patch is an ellipse shaped passageway 30 for receiving the far or distal end of an interior ribbon 32. In the passageway, the ribbon forms a generally ellipse shaped loop which constitutes the distal part of the patch delivery assembly or introducer 10. The passageway is shown in the preferred embodiment as a supplemental piece of patch material of a tubular fabric generally attached to the patch in the shape of an ellipse. The supplemental piece is preferably a tube coupled to the patch by stitches 34, or by glue or the like or may be fabricated in continuity in the patch. The coupling is at a location adjacent to the periphery of the patch and the periphery of the supplemental piece except at one end through which the ribbon extends. The ribbon preferably has a flat cross sectional configuration to promote its handling. Specifically, the longer flat face of the ribbon always extends parallel with the axis of the loop which it forms. Stability of the loop shape is enhanced which allows rotation of the ribbon during operation and use while maintaining such loop shape.

When distended, the loop 32 is in the form of an ellipse which has a major axis and a minor axis coextensive with the major axis and minor axis of the patch. In the alternative, the loop and its passageway may take one of the many other forms such as that of a teardrop, circle, oval or the like. Other smoothly shaped, curved configurations could be utilized. The periphery of the patch is at varying distances from the passageway and loop. Hence the peripheral portions of the patch may not necessarily immediately reach all the areas of direct as well as indirect hernias. Consequently, conventional laparoscopic techniques may be necessary by the surgeon to provide final positioning of the patch after initial expansion of the loop.

Located within the passageway is the loop of the ribbon 32, constructed of surgically antiseptic material and shaped in a smoothly curved configuration such as an ellipse when expanded and constrained by the passageway. The ribbon 32 is of a size and configuration to be received within the passageway of the patch 14. The loop exits at the distal end 38 of the intermediate plunger 42. As shown in the Figures, the loop of the ribbon holds the majority of the patch in an extended orientation for initial placement adjacent to the abdominal wall over the hernia to be repaired. The distal end of the ribbon is of a bullet shape, generally hemispherical, so as to facilitate smooth movement within the passageway. In the alternative, the endmost part of the ribbon could be simply bent inwardly toward the center of the patch to effect the same reult. The near or proximal end of the loop is a ribbon extension of the loop which, like the loop, is flexible, but sufficiently rigid to function in association with the plunger 42 so that a surgeon may remotely push, pull, or rotate the loop and, consequently, the patch, during an operation. The plunger 42 is a hollow cylinger through the ribbon passes. The introducer 10 includes the plunger 42 and a cylindrical exterior sheath 48.

The proximal end of the patch 14 includes an extension of the tubular component, the passageway 30, attaching to the distal end of the plunger so that the ribbon is at all time enclosed by the passageway. Coupling is preferably through a C-shaped spring clamp 52 installed at fabrication in a circular recess 54 on the plunger. Other coupling techniques include thread, glue, tape, or the like. Further, the attached tubular component could be coupled to the interior or end of the plunger. This coupling of patch and plunger assists the surgeon in the proper positioning of the patch on the area to be repaired.

Figure 3:
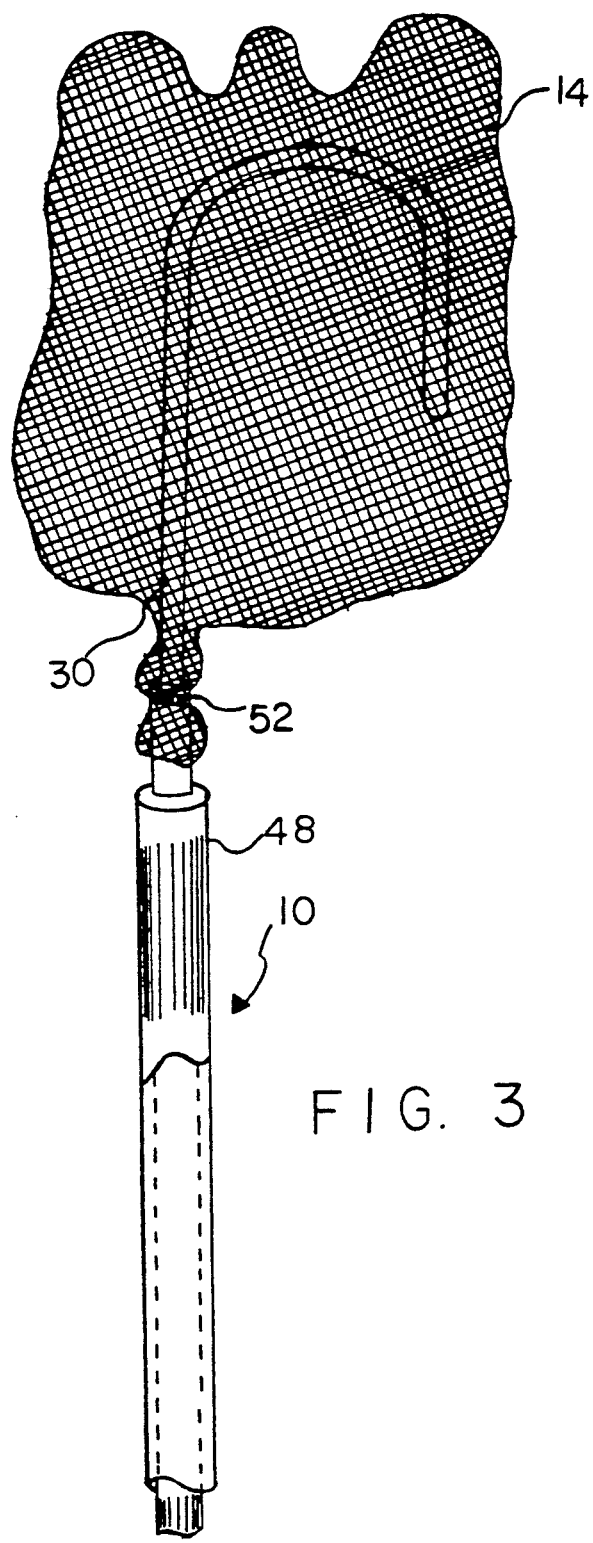
FIG. 3 is a sectional view of a portion of the patch and delivery system which is shown in FIG. 2.

The patch 14 as well as its supporting ribbon 32 and plunger and sheath are preferably prepackaged together as the delivery assembly 10, prior to use by insertion through a sleeve, channel or port which is conventionally placed in a patient by a trochar. The entire delivery assembly 10 is easily seen in FIGS. 3 and 4, sectional views.

Figure 4:
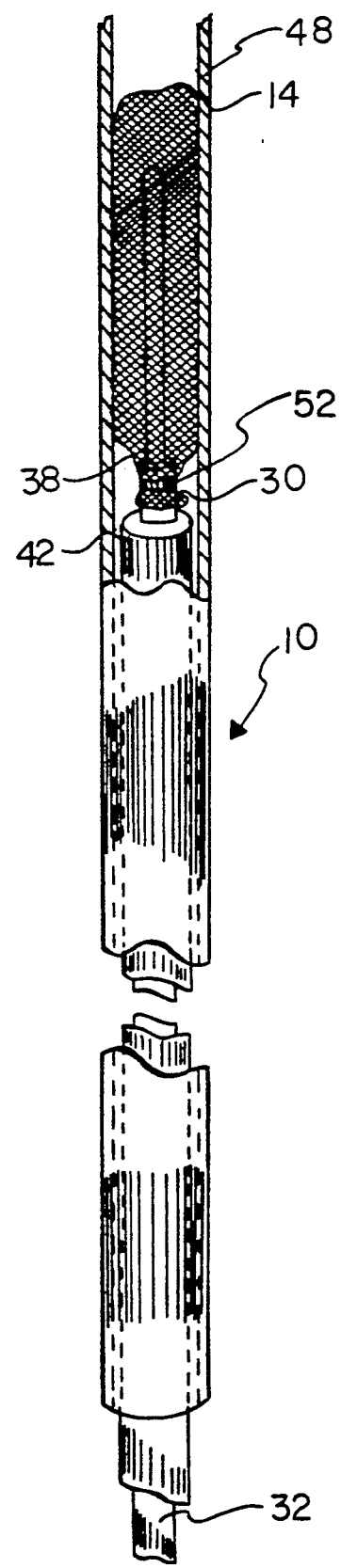
FIG. 4 is a sectional view of the delivery system of FIG. 2 but showing the patch in the sheath prior to deployment.

In operation and use, the introducer 10, patch, sheath, plunger and ribbon, is inserted through the channel in the patient with its distal end adjacent to the area of the abdominal wall to be patched. The patch 14 are prepositioned with in the sheath 48 as shown in FIG. 4. The introducer 10 then is moved forwardly by the surgeon moving the introducer with respect to the channel. The ribbon, loop and patch move with the introducer when relative movement occurs between the channel and introducer. The plunger is then moved forward from the sheath by either pushing the plunger forwardly with respect to the sheath or withdrawing the sheath with respect to the plunger. With the patch disposed out of the sheath, the ribbon is advanced with respect to the plunger to effect the positioning and orientation of the patch.

The passageway may be formed of a material which is impervious to the flow of air therethrough. In such embodiment, the expansion of the patch when exterior of the plunger is effected by a flow of air into the passageway of the patch prior to final positioning and attaching of the patch to the area to be repaired.

Using a second laparoscopic opening, the surgeon will position the edges of the patch into final position. Staples, sutures or clips are employed to secure the patch in its final position. The ribbon is then withdrawn from the passageway into the plunger. Thereafter, the passageway of the patch is cut adjacent to the distal end of the plunger to effect removal of the plunger and ribbon from the patient.

Markings in a grid pattern are preferably formed on the patch to ensure proper positioning and attachment to the patient. Additional markings are also preferably formed on the sleeve and ribbon to indicate the linear and rotational orientation of the sleeve and, hence, the patch. To that extent an axial marking on the sleeve extends proximally from the distal end to a location for indicating the proximal end of the patch. Any one or more or alternate markings could be utilized for these purposes. Such markings could be visually observable.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resortged to without departing from the spirit and scope of the invention.

Now that the invention has been described,

What is claimed is:

1. Laparoscopic apparatus for the repair of abdominal hernias by a surgeon through the patching of weakened portions of the abdominal part to be repaired comprising:

a patch formed of a flexible material positionable substantially in a plane adjacent to the weakened portions of the abdominal part to be repaired, the patch having an elongated passageway located in the plane of the patch adjacent to the majority of the periphery of the patch, the passageway having an opening at one end thereof;

an elongated interior ribbon having a distal end positioned through the opening of the passageway and freely slidable forwardly and rearwardly within the passageway, the ribbon being sufficiently rigid whereby it may be remotely pushed into the passageway;

an elongated intermediate cylindrical plunger having an interior slidably receiving the ribbon, the plunger having a distal end coupled to the patch and a proximal end to be manipulated by the surgeon; and an elongated exterior cylindrical sheath having an interior slidably receiving the plunger, the ribbon and the patch, the sheath having a distal end adjacent to the patch and a proximal end to be manipulated by the surgeon, the sheath being of a length to extend from exterior of a patient through a laparoscopic port into a surgical cavity which includes the part to be repaired.

2. Apparatus for use by a surgeon to repair a weakened, deranged portion of the anatomy of a patient comprising:

a sheath having a distal end positionable within a patient and a proximal end positioned exterior of the patient for manipulation by a surgeon, the sheath being of a length to extend from exterior of a patient through a laparoscopic opening into a surgical cavity of the patient;

a prothesis formed of flexible, essentially inextensible material movable from interior of the sheath to a generally planar orientation at a location adjacent to the deranged portion to be repaired, the prothesis having an elongated passageway located in the plane of the prothesis adjacent to the periphery thereof; and an introducer positioned within the sheath and having a distal end coupled to the prothesis, the introducer adapted to effect the movement of the prothesis from interior of the sheath to exterior thereof, said introducer including means therein, to expand the prothesis to a functionally expanded planar orientation adjacent to the portion to be repaired.

3. The apparatus as set forth in claim 2 wherein the prothesis is a patch.

4. The apparatus as set forth in claim 3 wherein the introducer means includes an elongated interior member having a distal end positioned through an opening in the passageway of the patch and freely slidable within the passageway, the interior member being sufficiently rigid whereby it may be remotely pushed into the passageway, the introducer also including an elongated intermediate cylindrical plunger having an interior slidably receiving the interior member, the plunger having a distal end coupled to the patch and a proximal end to be manipulated by a surgeon.

5. The apparatus as set forth in claim 4 wherein the interior member is a ribbon slidably removable from the patch.

6. A method for the laparoscopic repair of abdominal hernias by a surgeon through the patching of weakened portions of the abdominal part to be repaired comprising the steps of:

providing a patch formed of flexible, inextensible material and positionable in a plane adjacent to the weakened portions of the abdominal part to be repaired, the patch having an elongated passageway located in the plane of the patch adjacent to the majority of the periphery of the patch, the passageway having an opening at one end thereof;

providing an elongated interior ribbon having a distal end positioned through the opening of the passageway and slidable within the passageway, the ribbon being sufficiently rigid whereby it may be remotely pushed into the passageway;

providing an elongated intermediate cylindrical plunger having an interior slidably receiving the ribbon, the plunger having a distal end coupled to the patch and a proximal end to be manipulated by the surgeon;

providing an elongated exterior cylindrical sheath having an interior slidably receiving the plunger, the ribbon and the patch, the sheath having a distal end adjacent to the patch and a proximal end to be manipulated by the surgeon, the sheath being of a length to extend from exterior of a patient through a laparoscopic port into a surgical cavity which includes the part to be repaired;

positioning the patch and the distal ends of the ribbon, plunger and sheath into a patient adjacent to the area to be repaired;

advancing the patch and plunger from the sheath;

advancing the ribbon into the passageway of the patch to expand the patch;

coupling the patch to the area to be repaired;

withdrawing the ribbon from the patch;

separating the patch from the plunger; and withdrawing the ribbon, plunger and sheath from the patient.

* * * * *